United States Patent [19]

Vetter et al.

[11] 4,179,291
[45] Dec. 18, 1979

[54] PHOTOGRAPHIC DYE DIFFUSION TRANSFER PROCESS

[75] Inventors: Hans Vetter, Cologne; Paul Marx, Leverkusen, both of Fed. Rep. of Germany

[73] Assignee: AGFA-Gevaert, A.G., Fed. Rep. of Germany

[21] Appl. No.: 839,374

[22] Filed: Oct. 4, 1977

[30] Foreign Application Priority Data

Oct. 9, 1976 [DE] Fed. Rep. of Germany ....... 2645656

[51] Int. Cl.² .......................... G03C 1/40; G03C 5/54; G03C 7/00; G03C 1/10
[52] U.S. Cl. ..................................... 430/223; 430/958
[58] Field of Search ...................... 96/3, 29 D, 77, 99, 96/56.6

[56] References Cited

FOREIGN PATENT DOCUMENTS 2505248 8/1976 Fed. Rep. of Germany .

OTHER PUBLICATIONS

*Research Disclosure* #15654, Apr. 1977, pp. 32–39.

Primary Examiner—Richard L. Schilling
Attorney, Agent, or Firm—Connolly & Hutz

[57] ABSTRACT

In the dye diffusion transfer process for the production of colored images dye-providing compounds of the following formula give lower color fog values Dmin, as compared with known dye-providing compounds:

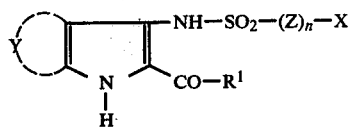

$X$ = dye or dye precursor
$Z$ = intermediate member
$n$ = 0 or 1
$R^1$ = $-O-R^2$; $-S-R^2$ or

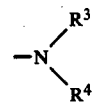

$R^2$ = hydrogen, alkyl, cycloalkyl or aryl
$R^3$ = a group as defined under $R^2$ or acyl
$R^4$ = hydrogen or alkyl
$Y$ = a residue to complete a condensed benzene ring and $R^1$ and/or a substituent on the condensed benzene ring is or contains a group that confers resistance to diffusion.

3 Claims, No Drawings

PHOTOGRAPHIC DYE DIFFUSION TRANSFER PROCESS

This invention relates to a process for the production of a colour photographic image by the dye diffusion transfer process and to a phtotgraphic material suitable for this process, which contains new diffusion resistant dye-providing compounds.

Among the known processes for the production of coloured photographic images by dye diffusion transfer, those based on the use of dye-providing compounds which are incorporated in a diffusion-fast form and from which diffusible dyes or dye precursors are split off in imagewise distribution during development and transferred to an image receiving layer are becoming of increased importance.

Dye-providing compounds suitable for such processes include, for example, the non-diffusible colour couplers described in German Patent No. 1,095,115. When development takes place, these colour couplers react with the oxidation product of a colour developer compound consisting of a primary aromatic amine, and as a result of this reaction, a preformed dye or a dye produced by the colour coupling reaction is released in a diffusible form. The choice of suitable developer compound for this process is, of course, restricted to colour developers. Other suitable dye-providing compounds are the non-diffusible compounds described in German Offenlegungsschrift No. 1,930,215. These compounds contain a preformed dye residue, which is potentially diffusible, attached by way of a removable hydrazone group to a residue which confers diffusion resistance. These compounds should not be regarded as colour couplers and it has been shown that the choice of developer compounds from which the necessary diffusible dye residue can be released is by no means restricted to the usual colour developers but may well be extended to black and white developers, e.g. pyrocatechol.

Non-diffusible coloured compounds which contain a special group have been described in German Offenlegungsschrift No. 1,772,929. These compounds undergo an oxidative ring closure reaction during development to release a preformed dye residue in a diffusible form. The compounds described in the said Offenlegungsschrift may be divided into two groups. The compounds of one group require a conventional colour developer compound for development so that they can couple with the oxidation product of this colour developer compound and then release the preformed dye residue in a diffusible form in a subsequent ring closure reaction. The compounds of the other group constitute silver halide developers and are therefore capable, when in their oxidized form, of undergoing the aforesaid ring closure reaction to release the diffusible dyes even in the absence of other developer compounds.

Lastly, the non-diffusible dye-providing compounds according to German Offenlegungsschrift No. 2,242,762 should also be mentioned here. These compounds are sulphonamido phenols and sulphonamido anilines. After the oxidation resulting from development, these compounds are decomposed by the alkali in the developer to release diffusible dyes, carrying a free sulphamoyl group.

All the dye-providing compounds mentioned above are negatively working compounds, that is to say if the usual (negative) silver halide emulsions are used, the diffusible dye which is liberated is distributed according to the negative silver image produced by development. The production of positive dye images therefore requires the use of direct positive silver halide emulsions or the use of a suitable reversal process.

In German Offenlegungsschrift No. 2,505,248 there has been described, inter alia, a derivative of 3-aminoindole as non-diffusible dye-providing compound for the dye diffusion process. This compound, compound 17, has an alkoxy substituted phenyl group in the 2-position of the indole ring. Although imagewise transfer of colour is achieved with the known compounds, these compounds are still not satisfactory with regard to the colour fog produced.

It is therefore an object of this invention to provide new non-diffusible dye-providing compounds which combine sufficient reactivity with the necessary stability, good colour transfer, high sensitivity and little fog.

The present invention relates to a photographic dye diffusion transfer process for the production of coloured images, in which process a photographic material having at least one light-sensitive silver halide emulsion layer and, associated with this layer, a non-diffusible dye-providing compound which in its oxidized form is capable of releasing a diffusible dye in the alkaline developer medium, is exposed imagewise and developed with a silver halide developer which, in its oxidized form, oxidizes the dye-providing compound, this oxidation resulting in decomposition of the said dye-providing compound by the developer alkali and imagewise distribution of the diffusible dye thereby liberated, characterised in that the non-diffusible dye-providing compound is represented by the following formula:

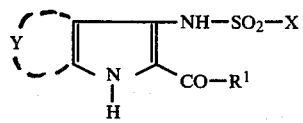

in which

X represents the residue of a dye or dye precursor attached to the $SO_2$ group either directly or by way of an intermediate member Z;

Z represents an intermediate member such as an alkyl(id)ene group having from 1 to 6 carbon atoms, arylene or a heterocyclic group which is connected to the group X either directly or by way of —O—, —S—, —$SO_2$—, —NR— (R=hydrogen or alkyl), —CO—, —CO—NH— or —$SO_2$—NH—;

Y represents a group for completing a condensed benzene ring, which ring may carry one or more substituents;

$R^1$ represents —$OR^2$—, —$SR^2$— or

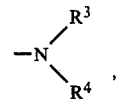

wherein $R^2$ represents hydrogen, an alkyl group having 1 to 22 carbon atoms such as a methyl, ethyl, isopropyl or n-octadecyl group, a cycloalkyl group such as a cyclohexyl group or an aryl group such as a phenyl group; the said alkyl, cycloalkyl and aryl groups may in turn be substituted, e.g. the alkyl groups may be substituted by hydroxyl, alkoxy, aroxy, halogen, carboxy or sulpho; the aryl groups may be substituted by halogen, alkyl, alkoxy, dialkylamino, acylamino, carboxyl or sulpho;

$R^3$ represents one of the groups mentioned under the definition for $R^2$ or it represents an acyl group derived from aliphatic or aromatic carboxylic or sulphonic acids;

$R^4$ represents hydrogen or a substituted or unsubstituted alkyl group having from 1 to 22 carbon atoms.

The condensed benzene ring completed by the group Y may be substituted one or more times, for example by substituents of the following kind: halogen, e.g. chlorine or bromine; alkyl having up to 22 carbon atoms, such as methyl, butyl or hexadecyl; aryl, e.g. phenyl, which may in turn be substituted, for example by halogen, alkyl, alkoxy, dialkylamino or acylamino; aralkyl, e.g. benzyl; cycloalkyl, e.g. cyclohexyl; alkoxy, e.g. methoxy, ethoxy, dodecyloxy or hexadecyloxy; aralkoxy, e.g. acylamino or acyl, which acyl group may be derived from aliphatic or aromatic carboxylic or sulphonic acids; cyano, sulpho, carboxyl, sulphamoyl or carbamoyl, one or two hydrogen atoms on the nitrogen atom of the carbamoyl or sulphamoyl group being optionally substituted, for example by alkyl groups; or the atoms required for completing a condensed isocyclic or heterocyclic ring. Where the condensed benzene ring completed by Y carries several substituents, these need not necessarily be identical. It should be noted that the dye-providing compounds according to the invention should not diffuse through the layers of photographic material when present as intact molecules. They contain a diffusion resistance conferring residue for this purpose, for example in the residue $R^1$ or in a substituent on the condensed benzene ring which is completed by Y.

The dye-providing compounds may be sufficiently resistant to diffusion even when $R^1$ and the substituents on the condensed benzene ring completed by Y do not contain long chain alkyl groups, because the molecule may even then be sufficiently large, depending on the size of the dye residue. In other cases, the dye-providing compounds may be rendered sufficiently diffusion resistant by suitable choice of sufficiently large diffusion resistance conferring residues.

Diffusion resistance conferring residues are residues which make it possible for the compounds according to the invention to be incorporated in a diffusion resistant form in the hydrophilic colloids normally used in photographic materials. The residues used for this purpose are preferably organic residues which generally contain straight or branched chain aliphatic groups and may also contain isocyclic or heterocyclic or aromatic groups generally having from 8 to 20 carbon atoms. These residues are attached to the remainder of the molecule either directly or indirectly, e.g. by way of one of the following groups: —NHCO—; —NHSO$_2$—; —NR—, wherein R represents hydrogen or alkyl; —O—; —S— or —SO$_2$—. The diffusion conferring residue may in addition contain groups which confer water solubility, e.g. sulpho groups or carboxyl groups; these water-solubilising groups may also be present in an anionic form. Since the diffusion properties depend on the molecular size of the compounds as a whole, it is sufficient in some cases, for example, when the molecule as a whole is large enough, to use relatively short chain groups as "diffusion resistance conferring residues".

The dye residues may in principle be residues of any series of dyes, provided they are sufficiently diffusible to be able to diffuse through the layers of the light-sensitive material to reach the image receiving layer. The dye residues may be provided with one or more water solubilizing groups for this purpose. The following, among others, are suitable water-solubilizing groups: Carboxyl groups, sulpho groups, sulphonamide or sulphamoyl groups and aliphatic and aromatic hydroxyl groups. The sulphamoyl group left in the dye after the splitting process itself imparts to the dye molecule a considerable tendency to diffusion in an alkaline medium, so that the presence of an additional water-solubilizing group is not always necessary. The following are mentioned as examples of dyes which are particularly suitable for the process according to the invention: Azo dyes, azomethine dyes, anthraquinone dyes, phthalocyanine dyes, indigoid dyes, triphenylmethane dyes and metal complex dyes or coloured metal complexes.

Residues of dye precursors are residues of compounds which are converted into dyes by the usual processing steps or by additional steps during the photographic process, either by oxidation or by coupling or by liberation of an auxochromic group in a chromophoric system, for example by saponification. Dye precursors in this sense may be leuco dyes, couplers or dyes which are converted into other dyes during photographic processing. Where it is not essential to distinguish between dye residues and the residues of dye precursors, the latter will hereinafter be included under the term "dye residues". The following are examples of suitable dye-providing compounds according to the present invention:

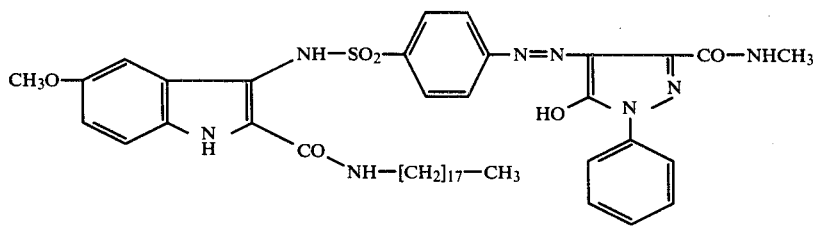

1

-continued
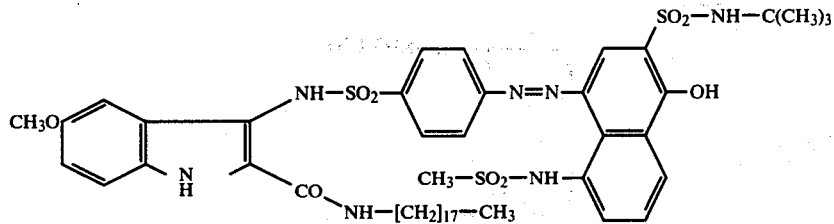
2
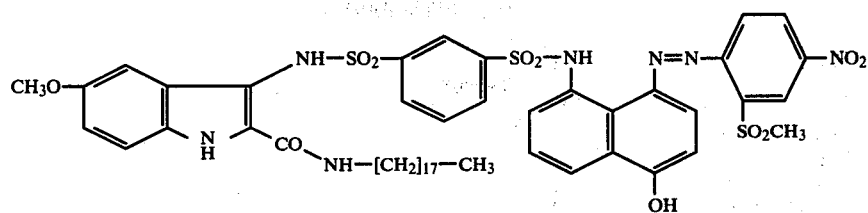
3
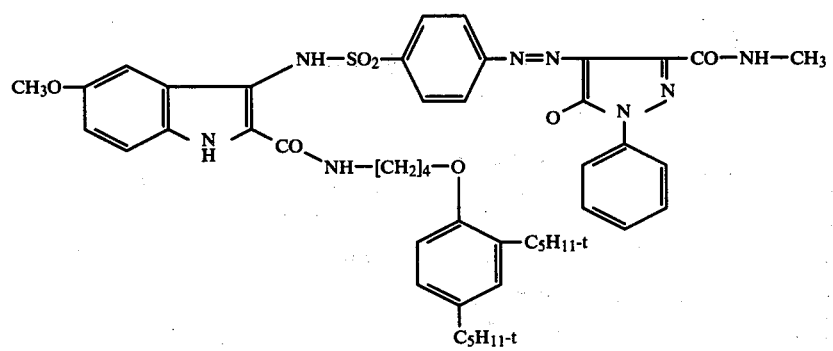
4
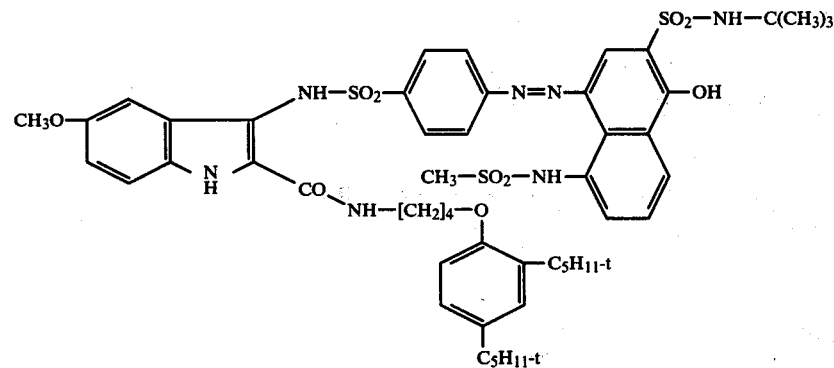
5
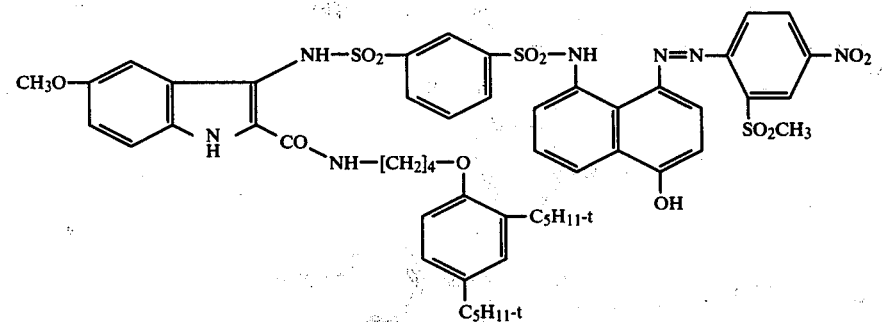
6
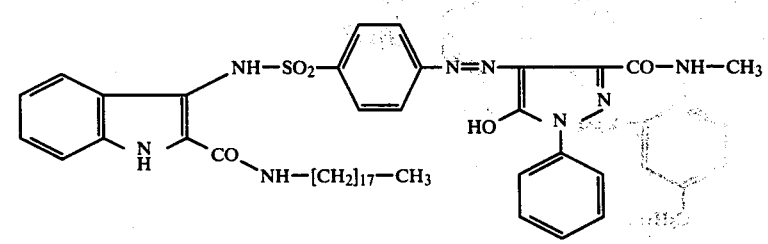
7

8
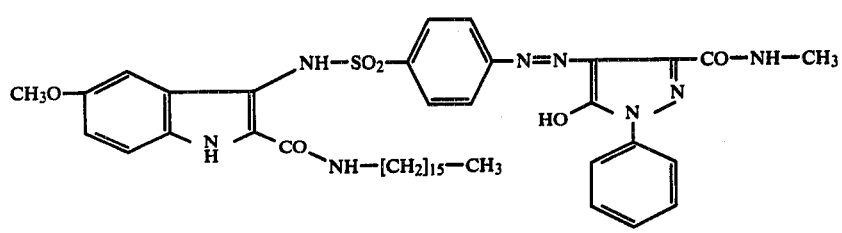
9
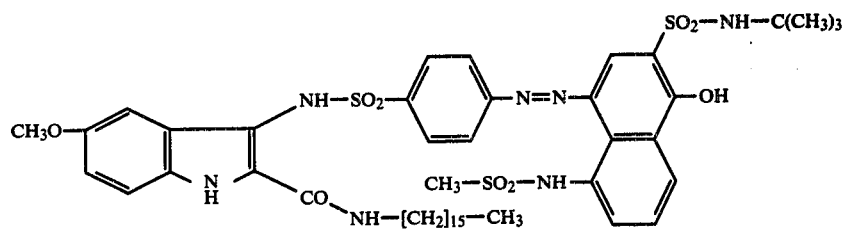
10
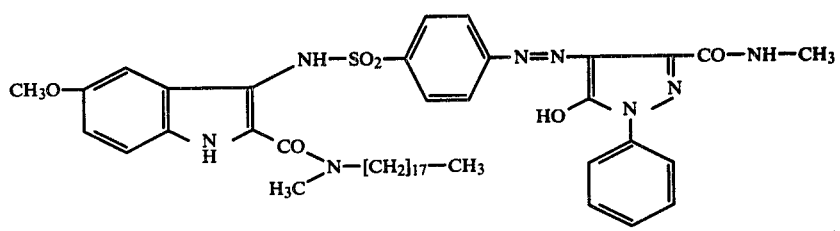
11
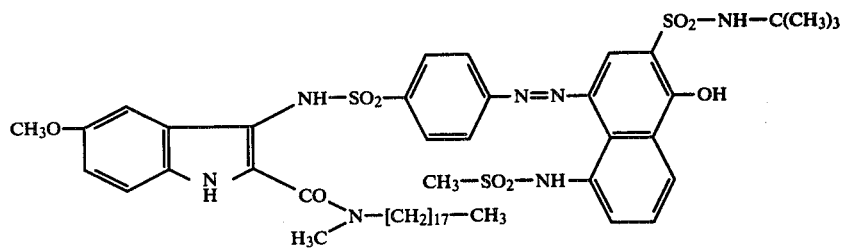
12
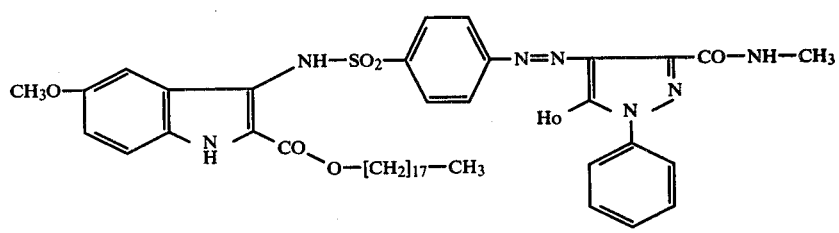
13
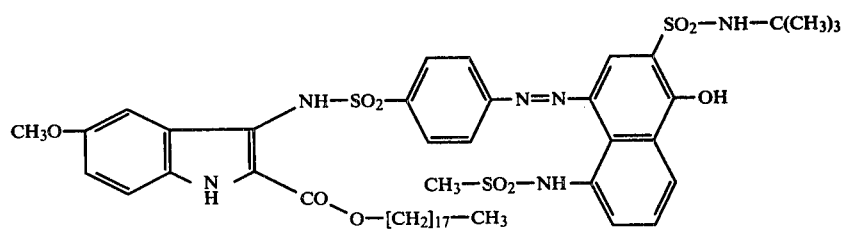
14
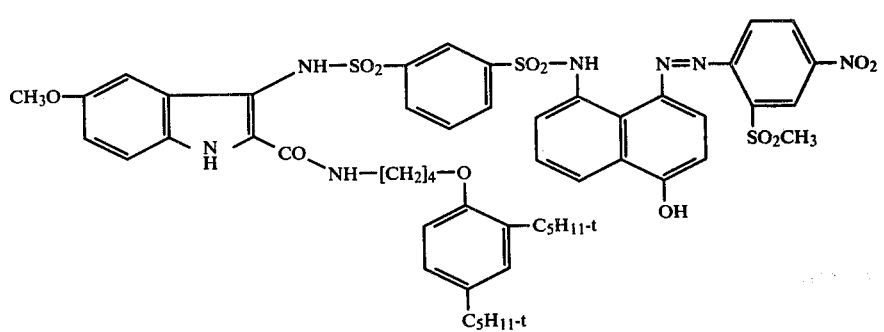

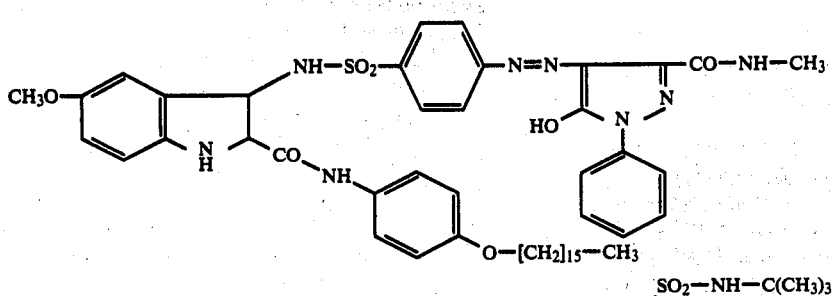

15

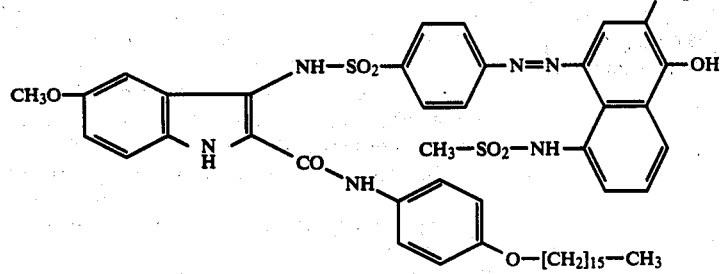

16

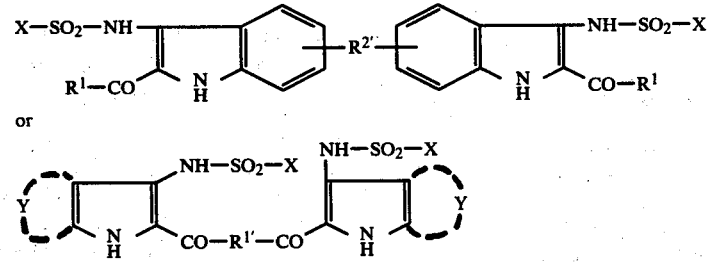

17

Where $R^1$ or a substituent on the condensed benzene ring of the indole group is divalent, e.g. $R^{1'}$ or $R^{2'}$, it may join two indole rings, for example as follows:

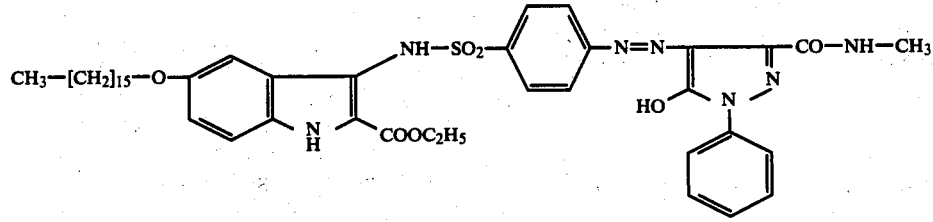

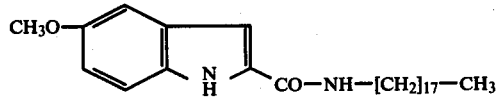

I

Preparation of the dye-providing compound 1

21.9 g of 5-methoxyindole-2-carboxylic acid ethyl ester are mixed with 29.6 g of octadecylamine in 200 ml of toluene, and 50 ml of toluene are distilled off. After cooling to 50° C., 3.65 ml of 30% sodium methylate solution are added and the reaction mixture is boiled under reflux for 5 hours. 475 ml of methanol are added dropwise without further heating while the mixture is still warm. The mixture is then cooled to 0° C. and the crystallisate formed is separated by suction filtration and washed with 200 ml of methanol. 37.2 g (corresponding to 84% of the theoretical yield) of compound I represented by the following formula melting at 139°–142° C. are obtained after drying.

37.2 g of compound I are dissolved in 375 ml of glacial acetic acid with mild heating, cooled to room temperature and added in small portions to 7.6 g of sodium nitrite over a period of one hour. Stirring is continued for one more hour and the reaction mixture is then briefly heated to 40° C. to bring the precipitated compound into a form which can be more easily removed by suction filtration. After cooling to 20° C., the mixture is suction filtered and the precipitate is washed, first with glacial acetic acid and then with plenty of water and dried. 39.6 g (corresponding to 99.7% of the theoretical yield) of compound II represented by the following formula

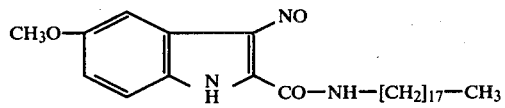

are obtained.

39.6 g of compound II are passed through a fine sieve and vigorously stirred in 370 ml of methanol. A solution of 41 g of sodium dithionite in 165 ml of water is poured all at once to the resulting slurry and the mixture is maintained at 60°–65° C. for 2 hours. It is then cooled to 20° C. and the residue is suction filtered and washed with 600 ml of 1% sodium dithionite solution. After drying, there are obtained 36 g (corresponding to 91% of the theoretical yield) of compound III represented by the following formula

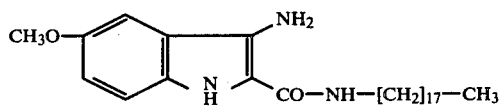

4.6 g of compound III are stirred in 50 ml of chloroform. 2 ml of pyridine are added, followed by 5.5 g of the dye sulphochloride represented by the following formula IV:

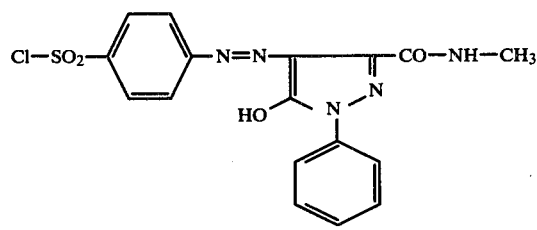

The mixture is stirred for one hour. 150 ml of methanol are added and stirring is continued for a further 3 hours. The precipitated dye is suction filtered. 4.4 g of compound 1 are obtained after drying. This compound is purified as follows: It is dissolved in 50 ml of warm chloroform. 100 ml of methanol are then added and the mixture is left to stand overnight. The compound which crystallises during this time is suction filtered, washed with methanol and dried. 2.8 g (corresponding to 33% of the theoretical yield) of dye-providing compound I are obtained.

Since numerous substituted indole-2-carboxylic acid esters as well as unsubstituted indole-2-carboxylic acid ethyl ester have been described in the literature, for example in the work by Heath-Brown and Philpott, in J. Chem. Soc. 1965, pages 7185–7193, other dye-providing compounds according to the invention may be obtained in a similar manner.

Other methods leading to the compounds according to the invention may, of course, also be employed. For example, suitable indole derivatives may be coupled with diazonium salts and reduced by known methods to the corresponding 3-aminoindoles and reacted with dye sulphochlorides to produce the compounds according to the invention.

The dye-providing compounds according to the invention are incorporated in the casting solutions for the layers of the photographic material by any of the usual methods. The quantity of dye-providing compound to be used per litre of casting solution varies within relatively wide limits. The most suitable concentration can easily be determined by simple tests. For example, 5 to 80 g, preferably 20 to 40 g, of dye-providing compound may be used per litre of casting solution. The correct positional relationship between the diffusion-fast dye-providing compound and the silver halide necessary for obtaining the desired effect can be achieved, for example, by introducing the diffusion-fast compounds into the casting solutions from aqueous-alkaline solution, making use of the water-solubilizing groups present. Alternatively, the non-diffusible, dye-providing compounds may be introduced into the layers by one of the known emulsification processes. Such processes have been described, for example, in British Patent Specifications No. 791,219 and Nos. 1,099,414, 1,099,415, 1,099,416 and 1,099,417. Another possible method consists of preparing an aqueous dispersion of the dye-providing compound and adding it to the casting solution. For this purpose, aqueous slurries of the dye-providing compound are finely milled, for example by vigorous stirring in the presence of sharp sand or by means of ultrasound. In another embodiment of this invention, for example, it may be desired to incorporate the dye-providing compounds in the layer in the form of so-called microcapsules together with silver halide and possibly also developer substances. Moreover, in such cases, two or more differently sensitized light-sensitive silver halide emulsions and the appropriate diffusion resistant compounds may be combined in a single layer as in so-called mixed grain emulsions which have been described, for example, in U.S. Pat. No. 2,698,794. The non-diffusible dye-providing compounds may be accommodated in a light-sensitive layer or in an adjacent layer. For example, a compound releasing a cyan dye may be associated with the red-sensitive layer, a compound releasing a magenta dye with the green-sensitive layer and a compound releasing a yellow dye with the blue-sensitive layer.

By "association" and "associated" is meant that the silver halide emulsion and dye-providing compound are arranged in such a manner in relation to each other that they can interact with each other to result in an imagewise correspondence between the silver image formed and the distribution of the released diffusible dye.

The associated dye-providing compound is preferably incorporated in the silver halide emulsion itself or in a layer adjacent to this silver halide emulsion layer, the said adjacent layer preferably being situated behind the silver halide emulsion layer, viewed in the direction of the incident light during exposure. When development of the silver image takes place, the dye-providing compounds according to the invention are oxidized imagewise by the oxidation products of the developer and then undergo a splitting reaction under the influence of the alkali of the developer or the activator, thereby releasing the dye residues in a diffusible form as dye sulphonamides, carrying a free sulphamoyl group. The usual photographic developer compounds may be used for development, providing they are capable, when in their oxidized form, of oxidizing the dye-providing compounds according to the invention.

The following are examples of suitable developers:
Hydroquinone;
N-methylaminophenol;
1-phenyl-3-pyrazolidone;
1-phenyl-4,4-dimethyl-3-pyrazolidone;

1-phenyl-4-methyl-4-hydroxymethyl-3-pyrazolidone;
1-phenyl-4,4-bis-hydroxymethyl-3-pyrazolidone; aminophenols;
N,N-diethyl-p-phenylenediamine;
N-ethyl-N-hydroxyethyl-p-phenylenediamine;
3-methyl-N,N-diethyl-p-phenylenediamine;
N,N,N',N'-tetraalkyl-p-phenylenediamines such as tetramethyl-p-phenylenediamine, triethylsulphobutyl-p-phenylenediamine and 1,4-bis-pyrrolidinobenzene; reductones.

It should be particularly mentioned that the choice of developer substance for the process according to the invention is not restricted to colour developers but may include the usual black-and-white developers; this is to be regarded as an advantage since the latter have a reduced tendency to discolouration.

The developers may be contained in the layers of the colour photographic material, where they are activated by the alkaline activator liquid; alternatively, they may be contained in the alkaline processing liquid or paste. Since the dye-providing compounds according to the invention themselves have developer properties, the use of auxiliary developer compounds may in some cases be dispensed with. In such cases, the dye-providing compound is directly oxidized by developable silver halide.

Since the imagewise distribution of diffusible dye released on development corresponds to the distribution of the developed silver image, direct positive silver halide emulsions are required for producing positive coloured transfer images or, if the usual negative emulsions are used, a suitable reversal process is necessary.

A suitable reversal process for this purpose is the silver salt diffusion process. Photographic reversal by means of the silver salt diffusion process to produce positive colour images by means of conventional colour couplers has been described, for example, in U.S. Pat. No. 2,763,800. If the colour couplers are replaced by the dye-providing compounds mentioned above, a light-sensitive element suitable for the dye diffusion transfer process is obtained. A light-sensitive element of this kind includes, for example, at least one combination of a light-sensitive silver halide emulsion layer and a layer of binder associated therewith, containing development nuclei for physical development and a dye-providing compound.

When development takes place, the exposed areas of silver halide in the light sensitive silver halide emulsion layer are chemically developed. The silver halide in the unexposed areas is transferred to the associated layer of binder containing development nuclei by means of a silver halide solvent and physically developed there. If physical development is carried out by means of a developer which, in its oxidized form is capable of releasing a diffusible dye as a result of a reaction with dye-providing compound present in this layer, this development results in an imagewise distribution of diffusible dyes which may be transferred to an image receiving layer to form a positive coloured image therein.

When reversal is carried out using compounds which release development inhibitors in imagewise distribution, the light-sensitive element comprises at least one combination of a light-sensitive silver halide emulsion layer and a second emulsion layer which is developable without exposure and which contains the dye-providing compound. The light-sensitive silver halide emulsion layer is developed, for example, with colour developers, in the presence of certain compounds which react with oxidized colour developer to release development inhibiting substances. The development inhibiting substances released imagewise in the light-sensitive layer diffuse into the adjacent emulsion layer which is developable without exposure, where they inhibit development imagewise. The uninhibited (positive) areas of the emulsion layer which is developable without exposure is developed by the remainder of the developer, whose oxidation products then react with the non-diffusible dye-providing compounds according to the invention to release diffusible dyes which are transferred imagewise to the image receiving element. Suitable compounds which release development inhibiting substances in their reaction with oxidation products of colour developers inclue, for example, the known DIR couplers (DIR=development inhibitor releasing) which are colour couplers containing a releasable inhibitor residue in the coupling position. DIR couplers of this type have been described, for example, in U.S. Pat. No. 3,227,554.

Another group of compounds which react with oxidation products of colour developers to release development inhibiting substances has been described in U.S. Patent No. 3,632,345. These are not colour couplers. No dyes are therefore formed when the development inhibitor substances are released. Lastly, according to German Pat. No. 1,229,389, suitably substituted nondiffusible hydroquinone compounds which are oxidized to the corresponding quinones by reaction with developer oxidation products and release development inhibiting mercaptans may be used in such a process.

The direct positive silver halide emulsions used may in principle be any silver halide emulsions which give rise to a positive silver image and a corresponding imagewise distribution of developer oxidation products when subjected to simple development. Silver halide emulsions of this kind include, for example, those in which a developable fog has been produced by exposure or chemical treatment, which fog is destroyed imagewise if certain conditions are observed during imagewise exposure. The fog is preserved in the unexposed areas so that subsequent development results in a direct positive silver image, and, corresponding therewith, an imagewise distribution of diffusible dye if a dye-providing compound according to the invention has been associated with the direct positive silver halide emulsion.

Another group of direct positive silver halide emulsions which are preferred according to the present invention comprises the so-called unfogged direct positive silver halide emulsions which have their sensitivity to light predominantly located in the interior of the silver halide grains. Imagewise exposure of these emulsions results in a latent image formed predominantly in the interior of the silver halide grains.

Development of such unfogged direct positive silver halide emulsions is, however, carried out under fogging conditions producing a fog mainly in the unexposed areas, and development produces a positive silver image. The unfogged direct positive silver halide emulsions are characterised in that when exposed samples are developed with a typical surface developer having the following composition:

| | |
|---|---|
| p-Hydroxyphenyl glycine | 10 g |
| Sodium carbonate (crystalline) | 100 g |
| made up with water to | 1000 ml | preferably no silver image is obtained or only one with a very low density, whereas an internal nuclear developer having the following composition:

| Hydroquinone | 15 g |
|---|---|
| Monomethyl-p-aminophenyl sulphate | 15 g |
| Sodium sulfate (anhydrous) | 50 g |
| Potassium bromide | 10 g |
| Sodium hydroxide | 25 g |
| Sodium thiosulfate (crystalline) | 20 g |
| made up with water to | 1000 ml | produces a sufficiently dense silver image.

The selective fogging of unfogged direct positive emulsions which have been exposed imagewise may be carried out by treating the emulsions with a fogging agent either before or during development. Reducing agents such as hydrazine or substituted hydrazines are suitable fogging agents. Reference may be made in this connection, for example, to U.S. Pat. No. 3,227,552.

Unfogged direct positive emulsion include, for example, those which contain faults in the interior of the silver halide grains (U.S. Pat. No. 2,592,250) or silver halide emulsions which have a layered grain structure (German Offenlegungsschrift No. 2,308,239).

The emulsions may also be chemically sensitized, for example by adding sulphur compounds such as allyl isothiocyanate, allylthiourea, sodium thiosulphate and the like at the chemical ripening stage. Reducing agents may also be used as chemical sensitizers, for example the tin compounds described in Belgian Pat. Nos. 493,464 and 568,687, polyamides such as diethylene triamine or aminomethane sulphinic acid derivatives, e.g. according to Belgian Pat. No. 547,323.

Noble metals such as gold, platinum, palladium, iridium, ruthenium or rhodium and compounds of these metals may also be used as chemical sensitizers. This method of chemical sensitization has been described in the article by R. Koslowsky, Z.Wiss.Phot. 46, 65–72 (1951).

The emulsions may also be sensitized with polyalkylene oxide derivatives, for example, with polyethylene oxide having a molecular weight of between 1000 and 20,000, or with condensation products of alkylene oxides and aliphatic alcohols, glycols, cyclic dehydration products of hexitols, alkyl substituted phenols, aliphatic carboxylic acids, aliphatic amines, aliphatic diamines and amides. The condensation products have a molecular weight of at least 700, preferably more than 1000. These sensitizers may, of course, be combined to produce special effects, as described in Belgian Pat. No. 537,278 and in British Pat. No. 727,982.

The emulsions may also be spectrally sensitized, for example with the usual monomethine or polymethine dyes such as acid or basic cyanines, hemicyanines, streptocyanines, merocyanines, oxonoles, hemioxonoles, styryl dyes or others, including trinuclear and higher nuclear methine dyes, for example rhodacyanines or neocyanines. Sensitizers of this kind have been described, for example, in the work by F. M. Hamer "The Cyanine Dyes and Related Compounds" (1964), Interscience Publishers John Wiley and Sons, New York.

The emulsions may contain the usual stabilizers, e.g. homopolar compounds or salt compounds of mercury having aromatic or heterocyclic rings, such as mercaptotriazoles, simple mercury salts, sulphonium mercury double salts and other mercury compounds. Azaindenes are also suitable as stabilizers, particularly tetra- and penta-azaindenes and especially those which are substituted with hydroxyl or amino groups. Compounds of this kind have been described in the article by Birr, Z.Wiss.Phot. 47, 2 to 27 (1952). Other suitable stabilizers include inter alia heterocyclic mercapto compounds such as phenylmercaptotetrazole, quaternary benzothiazole derivatives and benzotriazoles.

The biinder used for the photographic layers is preferably gelatine but this may be partly or completely replaced by other natural or synthetic binders. Suitable natural binders include e.g. alginic acid and its derivatives such as salts, esters or amides, cellulose derivatives such as carboxymethylcellulose, alkylcelluloses such as hydroxyethyl cellulose, starch or derivatives thereof such as ethers or esters, or carrageenates. Suitable synthetic binders include polyvinyl alcohol, partially saponified polyvinyl acetate and polyvinyl pyrrolidone and the like.

The layers may be hardened in the usual way, for example with formaldehyde or halogen substituted aldehydes containing a carboxyl group, such as mucobromic acid, diketones, methanesulphonic acid esters or dialdehydes.

For carrying out the dye diffusion transfer process according to the present invention, there is used a light-sensitive element containing one or more silver halide emulsion layers and the non-diffusible dye-providing compounds associated therewith and an image receiving element in which the desired colour image is produced by the diffusible dyes which have been transferred imagewise. Firm contact must be established between the light-sensitive element and the image receiving element for at least a finite period of time during development so that the imagewise distribution of diffusible dyes produced in the light-sensitive element as a result of development can be transferred to the image receiving element. This contact may be established after development has started or even before development has begun. The second method is employed if, for example, the material used for carrying out the dye diffusion transfer process is one in which the light-sensitive element and the image receptor element together form an integral unit, hereinafter referred to as monosheet material, which remains as a unit even after completion of the development process, that is to say the light-sensitive element is not separated from the image receiving element even after dye transfer has been completed. Such a process has been described, for example, in German Offenlegungsschrift No. 2,019,430.

A monosheet material suitable for carrying out the dye diffusion transfer process according to the present invention may contain, for example, the following layer elements:

(1) a transparent support layer
(2) an image receiving layer
(3) a light impervious layer
(4) a light-sensitive element having at least one light-sensitive silver halide emulsion layer and at least one non-diffusible dye-providing compound associated therewith
(5) a retarding layer
(6) an acid polymer layer
(7) a transparent support layer.

The monosheet material may be so arranged that two different parts are prepared separately from each other, namely the light-sensitive part (layer elements 1 to 4) and the cover sheet (layer elements 5 to 7), the two parts being subsequently placed together with their active surfaces facing each other and bonded together, optionally with the interposition of spacer strips to leave space between the two parts for an accurately measured quantity of processing liquid. The layer elements 5 and 6, which together constitute the neutralisation system, may, additionally or alternatively, also be arranged between the support layer and the image receiving layer of the light sensitive part, in which case, however, their sequence is reversed.

Means may be provided to introduce a processing liquid between the light-sensitive part and the cover sheet, for example in the form of a container which can be split open, this container being arranged at the side of the monosheet material so that it expels its contents between two adjacent layers of the monosheet material when subjected to mechanical forces.

An essential part of the photographic material according to the present invention is the light-sensitive element which, in the case of a monochrome transfer process, contains a light-sensitive silver halide emulsion layer and a non-diffusible, dye-providing compound associated therewith. This non-diffusible compound may be situated in a layer adjacent to the silver halide emulsion layer or in the silver halide emulsion layer itself. In the latter case, the colour of the image dye is preferably chosen so that the predominant absorption range of the dye-providing compound does not correspond with the predominant sensitivity range of the silver halide emulsion layer.

To produce multicoloured transfer images in true to life colours, however, the light-sensitive element contains three such associations of dye-providing compound and light-sensitive silver halide emulsion layer, and the absorption range of the dye-providing compound generally corresponds substantially with the range of spectral sensitivity of the associated silver halide emulsion layer. One precondition for obtaining as high a sensitivity as possible is that the colour producing combination should be arranged in a separate layer of binder behind (viewed in the direction of incident light during exposure) the silver halide emulsion layer.

The developer oxidation products resulting from development of a silver halide emulsion should, of course, only affect the associated dye-providing compound. Separating layers are therefore generally provided in the light-sensitive element to prevent diffusion of the developer oxidation products into other layers with which they are not associated.

These separating layers may, for example, contain suitable substances which react with the developer oxidation products, for example non-diffusible hydroquinone derivatives or, if the developer is a colour developer substance, a non-diffusible colour coupler. According to a preferred embodiment, therefore, the light-sensitive element has the following structure (from above downwards):

blue sensitive silver halide emulsion layer,
layer containing non-diffusible compound which releases a diffusible yellow dye,
separating layer,
green sensitized silver halide emulsion layer,
layer containing non-diffusible compound which releases a diffusible magenta dye,
separating layer,
red-sensitized silver halide emulsion layer,
layer containing a non-diffusible compound which releases a diffusible cyan dye.

The silver halide emulsion layers may, of course, be arranged in a different sequence, but the associated layers with colour producing systems must then also be interchanged so that the association is preserved.

The light-impervious layer arranged under the light-sensitive element is permeable to aqueous alkaline treatment solutions and hence to diffusible dyes. It has two main functions: First, it serves to cover the image silver remaining in the original light-sensitive element after development as well as the dye-providing compounds remaining behind as colour negative so that when the photographic material is viewed through the transparent support layer of the light-sensitive part, only the positive colour transfer image is visible; second, it shields the light-sensitive element against light from the side of the image receiving layer (from the bottom). This is particularly important if the monosheet material is to be brought into contact with the alkaline processing substance while still inside the camera after exposure and is then to be pulled out of the camera and developed outside the camera.

Layers which are sufficiently impervious to light but sufficiently permeable to diffusible dyes may be prepared, for example, from suspensions of inorganic or organic dark pigments, preferably black pigments, for example suspensions of carbon black, in suitable binders, e.g. in gelatine solutions. Layers from 0.5 to $2\mu$ in thickness containing from 10 to 90% by weight, based on the total dry weight, of carbon black in gelatine are generally sufficient to ensure adequate exclusion of light during development. The particle size of the pigments used is relatively uncritical provided that it does not substantially exceed $0.5\mu$.

In addition to the layer of black pigment, the light impervious layer preferably includes another layer of white pigment arranged underneath the latter. The object of this white pigment layer is to cover the black layer and provide a white background for the image. Any white pigments are suitable for this purpose, provided that they have sufficient covering power in not unduly thick layers. The following are examples: Barium sulphate, oxides of zinc, titanium, silicon, aluminium and zirconium, barium stearate and kaolin. The white pigment used is preferably titanium dioxide. The same conditions with regard to binder, concentration and particle size apply as for the black pigments. The thickness of the white pigment layer may be varied according to the desired degree of whiteness of the background. Thicknesses of between 5 and $20\mu$ are preferably employed.

Instead of providing a light-impervious layer in the monosheet material according to the present invention, means for producing such a light impervious layer may be arranged between the light-sensitive element and the image receiving layer, for example in the form of a container arranged at the side of the monosheet material and containing a clouding agent (pigment) which is released when the container is subjected to mechanical forces, and is distributed between the aforesaid layers to form a pigment layer of the kind described above.

The image receiving layer consists substantially of a binder containing dye mordants for fixing the diffusible dyes.

The mordants used for acid dyes are preferably long chain quaternary ammonium or phosphonium compounds or ternary sulphonium compounds, for example those described in U.S. Pat. Nos. 3,271,147 and 3,271,148. Certain metal salts and their hydroxides which form sparingly soluble compounds with the acid dyes may also be used. The dye mordants are dispersed in one of the usual hydrophilic binders in the image receiving layer, e.g. in gelatine, polyvinyl pyrrolidone or partly or completely hydrolysed cellulose esters. Some binders may, of course, also function as mordants, for example, copolymers or polymer mixtures of vinyl alcohol and N-vinylpyrrolidone such as those described, for example, in German Auslegeschrift No. 1,130,284, or those which constitute polymers of basic quaternary nitrogen compounds, e.g. polymers of N-methyl-2-vinylpyridine, for example as described in U.S. Pat. No. 2,484,430. Other suitable mordanting binders include, for example, guanyl hydrazone derivatives of acyl styrene polymers, for example, as described in German Offenlegungsschrift No. 2,009,498. In general, however, other binders, e.g. gelatine, would be added to the last-mentioned mordanting binders.

The transparent support layers used for the monosheet material according to the invention may be the transparent support materials commonly used in photography, for example films of cellulose esters, polyethylene terephthalate, polycarbonate or other film-forming polymers. The alkaline processing mass adjusts the light-sensitive material to a relatively high pH (approximately 11 to 14), which releases development and image-wise dye diffusion. It has been found that at these high pH values, the dyes and hence the images obtained are not particularly stable. The material must therefore be adjusted to almost neutral or slightly acid after development has been completed. This can be achieved in known manner by incorporating in the material an additional, acid polymer layer which becomes accessible to the alkaline processing mass only gradually during development. By "acid polymer layer" is meant a layer of binder containing polymeric compounds which have acid groups, preferably sulpho or carboxyl groups. These acid groups react with the cations of the processing substance to form salts and thereby lower the pH of the substance. The polymeric compounds, and hence the acid groups, are, of course, incorporated in a diffusion-fast form in their layer. The acid polymers are in many cases derivatives of cellulose or polyvinyl compounds but other polymer compounds may also be used. The following are examples of suitable acid polymers: Cellulose derivatives having a free carboxyl group, e.g. cellulose dicarboxylic acid semiesters having a free carboxyl group, such as cellulose acetate hydrogen phthalate, cellulose acetate hydrogen glutarate, ethyl cellulose acetate hydrogen succinate, cellulose acetate hydrogen succinate hydrogen phthalate, esters and esters of cellulose modified with dicarboxylic acid anhydrides or with sulphonic acid anhydrides, for example with o-sulphobenzoic acid anhydride; carboxymethyl cellulose; polystyrene sulphonic acid; polyvinyl hydrogen phthalate; polyvinyl acetate hydrogen phthalate; polyacrylic acid; acetals of polyvinyl alcohol with aldehydes which are substituted with carboxyl or sulpho groups, such as o-, m- or p-benzaldehyde sulphonic or carboxylic acid; partially esterified ethylene/maleic acid anhydride copolymers and partially esterified methyl vinyl ether/maleic acid anhydride copolymers.

The acid polymer layer must contain sufficient acid groups to lower the pH of the processing substance from the initial value of from 11 to 14 so that the material will finally be almost neutral or slightly acid (pH 5 to 8). The time delay in reducing the pH is obtained in known manner by coating the acid polymer layer with a so-called retarding layer. This retarding layer is a layer which is impervious to alkali and preferably consists of a polymer which is inert towards alkalies, for example polyvinyl alcohol or a partially acetalised polyvinyl alcohol. The amount of time delay in lowering of the pH can be adjusted as described by suitable choice of the thickness and composition of this retarding layer. A barrier layer containing polymers having a new type of permeability behaviour has been described, for example, in U.S. Patent Application Ser. No. 633,801, filed Oct. 20, 1975 or U.K. Pat. application No. 44 909/75 or in German Offenlegungsschrift No. 2,455,762.

Neutralisation systems, that is to say combinations of an acid polymer layer with a retarding layer, have been described, for example, in German Pat. No. 1,285,310. The material according to the invention may contain such layer combinations, for example in the light-sensitive part, between the transparent support layer and the image receiving layer.

Another possible method of retarding the change in pH consists of arranging a neutralisation system of acid polymer layer and retarding layer on the cover sheet. These two layers must, of course, be arranged in such a sequence that the alkali of the processing substance must first penetrate the retarding layer before it can reach the acid polymer layer.

The dye diffusion transfer process according to the invention may advantageously be carried out in or by means of a suitable self developer camera. This camera may be equipped, for example, with devices by means of which a solution can be distributed between the light-sensitive element and the cover sheet after the light-sensitive element has been exposed, thereby shielding the light-sensitive material against light from the top. Such a camera preferably has a pair of squeezing rollers between which the monosheet material is pulled out so that the containers arranged at the side of the material are split open to release their contents between the appropriate layers of the monosheet material.

Since the light-sensitive element is protected against unwanted exposure on both sides by light impervious layers after it has passed through the squeezing rollers, it may be pulled out of the camera immediately after development has been started.

To process the monosheet material after it has been exposed imagewise, the light-sensitive element is brought into contact with the aqueous alkaline processing solution. The silver halide emulsion layers which have been exposed imagewise are thereby developed in the presence of the developer compound, and an imagewise distribution of oxidation products of the developer compound is produced in correspondence with the positive silver image produced by development. These oxidation products oxidize the associated dye-providing compound, whereupon the oxidized dye-providing compound reacts with the alkali of the activator to release the diffusible dye.

The aqueous alkaline processing solution may contain viscosity increasing additives, e.g. hydroxyethylcellulose. It may also contain known development accelerators, stabilizers, silver salt solvents, fogging agents, anti-oxidants and other additives.

EXAMPLE 1

A light-sensitive element of a photographic material according to the invention was prepared by applying the following layers in succession to a transparent polyester foil serving as support. The quantities given refer to 1 m².
(1) A mordanting layer of 5.71 g of a copolymer of 400 g of diphenylmethane diisocyanate, 150 g of N-alkyldiethanolamine and 90 g of epichlorohydrin (according to Example 1 of German Offenlegungsschrift No. 2,631,521) and 5.8 g of gelatine;
(2) a reflection layer of 27 g of titanium dioxide and 2.7 g of gelatine;
(3) a carbon black layer of 1.85 g of carbon black and 2 g of gelatine;
(4) a dye layer composed of 0.45 g of compound 1 and 0.75 g of gelatine;
(5) a sensitized emulsion layer containing an unfogged direct positive silver iodochlorobromide emulsion, silver application 2.63 g, 1 mg of 1-(3'-carboxyphenyl)-5-mercapto-tetrazole, 66 mg of octadecylhydroquinone sulphonic acid, 4 mg of acetylphenyl hydrazine and 1.3 g of gelatine;
(6) a protective layer of 2.6 g of gelatine.

A strip of the light-sensitive element was exposed through a stepped wedge. After attachment of a breakable bag containing paste to one end and two spacer strips 180μ in thickness to the sides of the light-sensitive element, the element was covered with a polyester foil. The resulting set was passed through the nip between a pair of squeezing rollers so that the developer paste was distributed between the light-sensitive element and the cover sheet. The developer used was a paste having the following composition:

20 g of potassium hydroxide
10 ml of benzyl alcohol
1 g of paraformaldehyde
3 g of benzotriazole
0.25 g of ascorbic acid
1.3 g of 4-hydroxymethyl-4-methyl-phenidone
0.1 g of hydroquinone
30 g of hydroxyethylcellulose made up with water to 1000 ml.

The image element was separated after a development time of 10 minutes and freed from paste still adhering to it. A positive magenta image was visible through the transparent substrate, the titanium dioxide layer serving as background for the image.

EXAMPLE 2

The process described in Example 1 was repeated except that in this case compound 1 in layer 4 was replaced by compounds 2 to 5, 8, 9 and comparison compounds I to VIII. After the same method of processing as in Example 1, positive magenta, yellow or cyan dye transfers, respectively, were obtained. The results, including the result obtained with compound 1, are summarized in the following Tables. These show that the compounds according to the invention provide substantially improved fog values $D_{min}$.

The dyes indicated by arabic numerals are dyes according to the invention. The formulae of dyes numbered with Roman numerals are shown in the annexe to this Example. Dyes I, II, III, VII and VIII are those obtained by the state of the art disclosed in German Offenlegungsschrift No. 2,505,248. Dyes IV, V and VI correspond to the state of the art disclosed in German Offenlegungsschrift No. 2,242,762.

Magenta dyes

| Dye No. | $D_{min}$ | $D_{max}$ |
| --- | --- | --- |
| VI | 0.43 | 1.78 |
| V | 0.48 | 2.29 |
| VIII | 0.52 | 1.69 |
| II | 0.58 | 1.75 |
| VII | 0.66 | 1.85 |
| 2 | 0.26 | 2.03 |
| 5 | 0.27 | 2.12 |
| 9 | 0.22 | 1.90 |

Yellow dyes

| Dye No. | $D_{min}$ | $D_{max}$ |
| --- | --- | --- |
| IV | 0.59 | 1.64 |
| I | 0.57 | 1.49 |
| 4 | 0.33 | 1.54 |
| 8 | 0.38 | 1.37 |
| 1 | 0.30 | 1.67 |

Cyan dyes

| Dye No. | $D_{min}$ | $D_{max}$ |
| --- | --- | --- |
| III | 0.87 | 1.94 |
| 3 | 0.24 | 1.84 |

Comparison dyes:

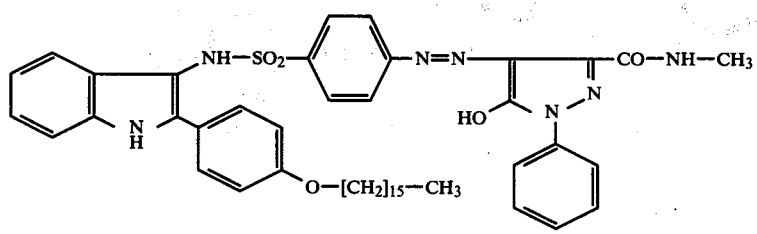

I

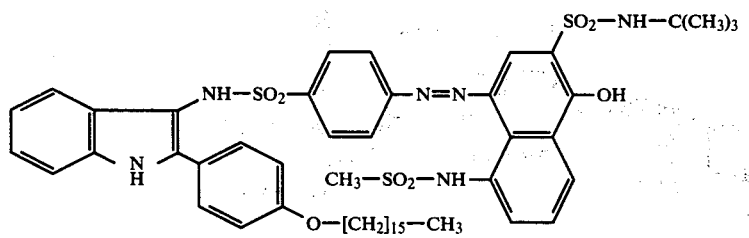

II

-continued
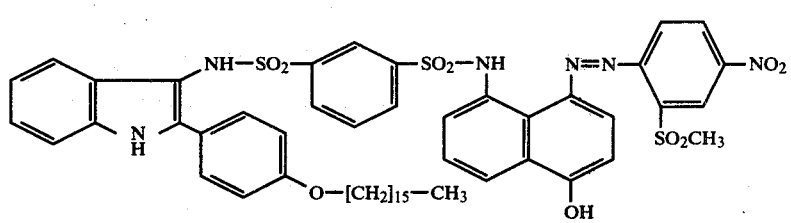
III
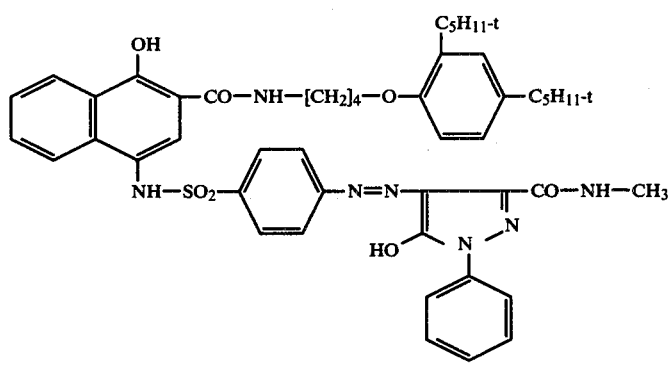
IV
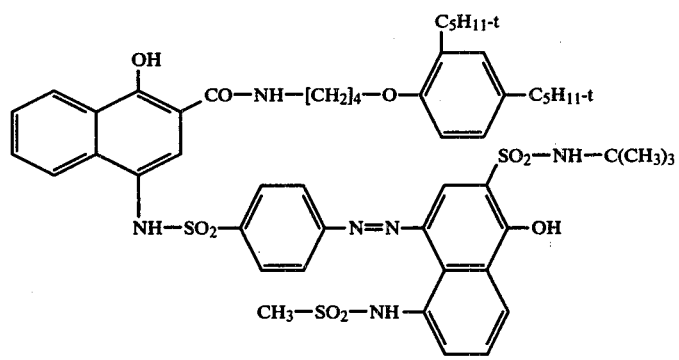
V
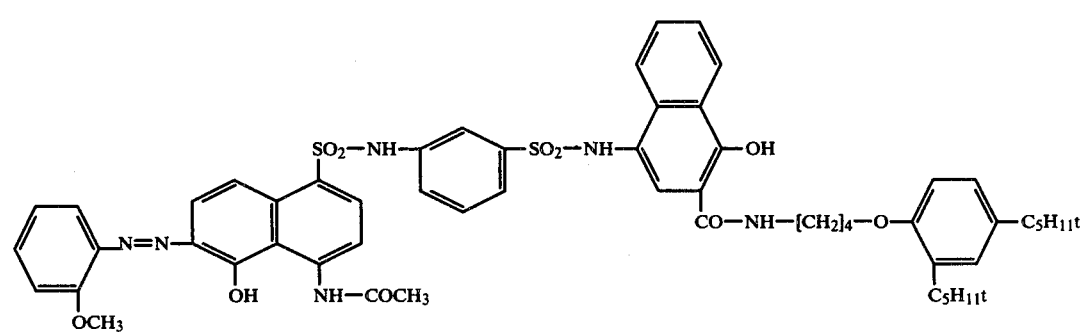
VI
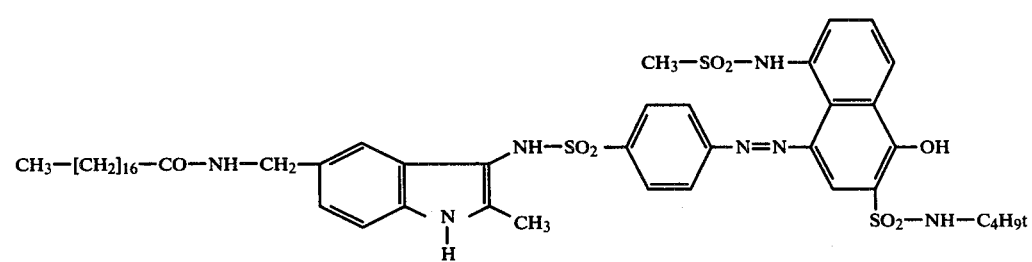
VII -continued

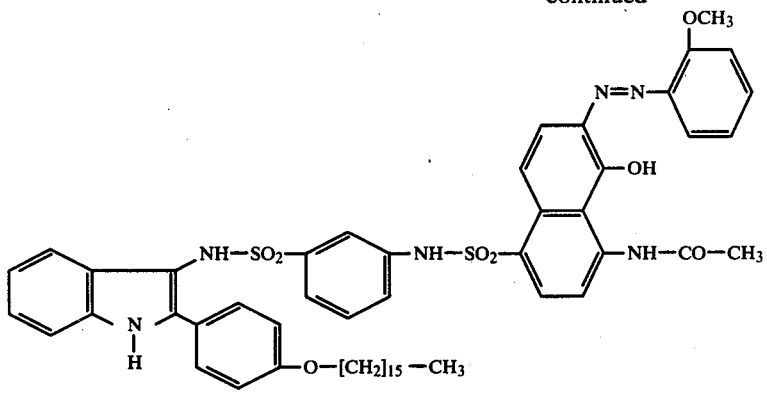
VIII

We claim:

1. The photographic dye diffusion transfer process for the production of colored images, in which a photographic material comprising at least one light-sensitive silver halide emulsion layer and, associated therewith, a non-diffusible dye-providing compound which in its oxidized form is capable of releasing a diffusible dye in an alkaline medium, is exposed imagewise and developed with a silver halide alkaline developer which in its oxidized form oxidizes the non-diffusible dye-providing compound and the latter is split by the developer alkali as a consequence of this oxidation, releasing a diffusible dye in image distribution, in which the improvement comprises the non-diffusible dye-providing compound is represented by the following formula:

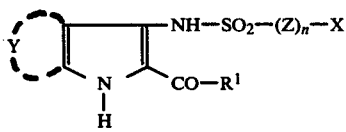

in which
X represents the residue of a dye precursor which is attached to to the $SO_2$ group either directly or by way of an intermediate member Z;
Z represents an alkylene group with 1 to 6 carbon atoms, arylene or a heterocyclic group which is attached to the residue X either directly or by way of an —O—, —S—, —$SO_2$—, —NR— (R=hydrogen or alkyl), —CO—, —CO—NH— or —$SO_2$—NH—group;
n is 0 or 1;
Y represents the residue to complete a condensed benzene ring;
$R^1$ represents —$OR^2$—, or

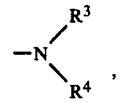

$R^2$ represents hydrogen, an alkyl group having from 1 to 22 carbon atoms, or a cycloalkyl or aryl group; the said alkyl, cycloalkyl and aryl groups may in turn be substituted;
$R^3$ represents one of the residues given under the definition for $R^2$ or an acyl group derived from aliphatic or aromatic carboxylic or sulphonic acids;
$R^4$ represents hydrogen or a substituted or unsubstituted alkyl group having from 1 to 22 carbon atoms; and in which $R^1$ and/or a substituent on the condensed benzene ring which is completed by Y represents or contains a residue which confers diffusion resistance.

2. The process as claimed in claim 1 in which the condensed benzene ring which is completed by Y contains one or more identical or different substituents selected from the group consisting of halogen, alkyl having up to 22 carbon atoms, aryl, aralkyl, cycloalkyl, alkoxy, aralkoxy, hydroxyl, dialkylamino, acylamino, acyl, cyano, sulfo, carboxyl, sulfamoyl, carbamoyl and residues for completing a condensed carbocyclic or heterocyclic ring.

3. The process as claimed in claim 2 in which the condensed benzene ring completed by Y is substituted by a methoxy or ethoxy group.

* * * * *